(12) United States Patent
Gott et al.

(10) Patent No.: US 6,733,766 B2
(45) Date of Patent: May 11, 2004

(54) PERSONAL CARE COMPOSITION WITH COLOR CHANGE INDICATOR

(75) Inventors: Robert Edward Gott, Norwalk, CT (US); Ewa Urszula Padlo, Derby, CT (US); Craig Stephen Slavtcheff, Guilford, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 121 days.

(21) Appl. No.: 10/139,808

(22) Filed: May 6, 2002

(65) Prior Publication Data

US 2003/0206878 A1 Nov. 6, 2003

(51) Int. Cl.⁷ .................................................. A61K 7/00
(52) U.S. Cl. ........................ 424/401; 514/844; 514/846
(58) Field of Search .................... 424/401; 510/130, 510/418; 514/844, 846

(56) References Cited

U.S. PATENT DOCUMENTS

| | | |
|---|---|---|
| 5,357,989 A | 10/1994 | Gathani |
| 5,665,368 A | 9/1997 | Lentini et al. |
| 5,747,011 A | 5/1998 | Ross et al. |
| 5,804,203 A | 9/1998 | Hahn et al. |
| 6,007,797 A | 12/1999 | Bell et al. |
| 6,060,072 A | 5/2000 | Konik et al. |
| 6,086,858 A | 7/2000 | McEleney et al. |
| 6,099,825 A | 8/2000 | McShane et al. |
| 6,146,618 A | 11/2000 | Bell et al. |
| 6,270,783 B1 | 8/2001 | Slavtcheff et al. |
| 6,290,936 B1 | 9/2001 | Ross et al. |
| 6,309,655 B1 | 10/2001 | Minnix |

FOREIGN PATENT DOCUMENTS

| | | |
|---|---|---|
| WO | 98/58628 | 12/1998 |
| WO | 01/12150 | 2/2001 |

OTHER PUBLICATIONS

Copy of Biore self–heating mask package—1998.
International Search Report.

Primary Examiner—Shelley A. Dodson
(74) Attorney, Agent, or Firm—Milton L. Honig

(57) ABSTRACT

A substantially dry composition, especially for personal care products is provided which includes a colorant activatable in water to release a visual color, and an oil-soluble carrier. The colorant is insoluble in the carrier and the visual color is not imparted to the composition in its substantially dry state. Addition of water to the composition activates a color change which renders the visual color perceivable by a consumer. Color changes can be associated as a signal of performance by a consumer.

14 Claims, No Drawings

PERSONAL CARE COMPOSITION WITH COLOR CHANGE INDICATOR

BACKGROUND OF THE INVENTION

1. Field of the Invention

The invention relates to personal care products, especially cleansers, which develop color when the compositions are combined with water.

2. The Related Art

Consumers often measure efficacy of a personal care product through some physically perceivable sensorial signal. Skinfeel of a product is one of the most common signals. Silky, non-residue leaving cosmetics are much preferred over tacky ones, and consumers may relate those aesthetics to actual pharmacological performance.

Temperature may operate as a sensorial signal. Coolness can be imparted to toothpastes, aftershave lotions and shower gels through the presence of camphor, menthol or menthol releasing derivatives. Some formulations signal efficacy through a temperature increase. Inclusion of capsaicin gives a brief temperature rise sensation to the human neural system. Exothermic and endothermic reactions are other sources of temperature signaling. U.S. Pat. No. 6,270,783 B1 (Slavtcheff et al.) and WO 01/12150/A1 (Mohammadi) illustrate interactive effects of temperature changes in combination with color generation.

Products by Schering-Plough Healthcare Products, Inc. and related patents introduced a sunscreen lotion with an indicator brightly colorizing the lotion until applied to the human skin. Upon rub-in, the lotion decolorizes or turns clear. A user of the product can through visual means ensure even distribution of the sunscreen over the body. The mechanism is based upon an aqueous system with a pH sensitive indicator. On the skin, water from the lotion evaporates altering pH and eventually decolorizing the applied product. See U.S. Pat. No. 6,086,858 (McEleney et at.), U.S. Pat. No. 6,007,797 (Bell et al.), U.S. Pat. No. 6,146,618 (Bell et al.), U.S. Pat. No. 6,099,825 (McShane et al.), U.S. Pat. No. 6,290,936 B1 (Ross et al.), and U.S. Pat. No. 5,747,011 (Ross et al.).

Use of pH indicators has also been incorporated into a dental floss. See U.S. Pat. No. 5,357,989 (Gathani).

Another commercial embodiment of a color change signal is Biore® Self Heating Mask. The product lists the following ingredients: butylene glycol, sodium silico aluminate, kaolin, PEG-8, methyl gluceth-20, hydroxypropyl cellulose, dimethicone, hydroxypropyl methylcellulose, talc, acrylates copolymer, polyethylene and minor ingredients including encapsulated ultramarine pigments. Instructions on use of the product require wetting of the face which when contacted with the Biore® product causes self-heating by reaction of water with the silico aluminates and kaolin. The composition is applied by rubbing across the face. Massage through the rubbing action breaks the encapsulating material, releasing the ultramarine pigments thereby turning the composition a uniform blue color. Once developed, the blue color signals the consumer it is time to rinse away the product. Further information on this product appears in U.S. Pat. No. 6,309,655 B1 (Minnix). A drawback of this system is the requirement for actual physical breakdown of walls encapsulating the colorant. This procedure is messy and requires an active manipulation. Furthermore, blue beads are visible (ranging from greater than 200 to 800 microns) in the starting Biore® product even before application and wider release of the pigments.

New mechanisms for color change signals have been sought which are less restrictive than those of the known art.

Accordingly, it is an advantage of the present invention to be able to provide personal care products, with a color sensorial signal change.

Another advantage of the present invention is to be able to provide personal care products, especially non-lathering creamy cleansers which change from white to another color after the product is combined with water.

These and other advantages of the present invention will become more readily apparent from consideration of the following summary and detailed discussion.

SUMMARY OF THE INVENTION

A personal care, substantially dry composition is provided which includes:

(i) a colorant activatable in water to reveal a visual color; and (ii) an oil soluble carrier;

wherein the colorant is insoluble in the carrier and does not impart the visual color to the composition in its substantially dry state.

DETAILED DESCRIPTION

Now it has been found that a color signal can be generated from a substantially dry composition that is an oil soluble carrier formulated with a water soluble inorganic or organic colorant. In the substantially dry state, the composition receives no color contribution from the colorant. However, once a consumer mixes water into the composition, such as in a skin cleansing process, a color change occurs.

The starting color of compositions according to this invention may essentially be any color. However, most preferred is a white or slightly off-white color, usually imparted by an opacifier such as titanium dioxide. Colorants when present as beads may be of a color different from that of the initial color. However, a consumer will essentially not perceive the bead or its color because of its small size. Thus, colorants that may be present in bead form will have an average particle size ranging from about 0.0001 to about 200 $\mu$m, preferably no higher than about 150 $\mu$m, more preferably no higher than about 100 $\mu$m, optimally no higher than about 50 $\mu$m. Advantageously, no more than 30% of the colorant beads should have a particle size greater than 200 $\mu$m, preferably not more than 150 $\mu$m.

Accordingly, an important element of the present invention is that of an oil soluble carrier which is a hydrophobic system of one or more components having a weighted arithmetic mean solubility parameter of less than or equal to 10.5. It is recognized, based on this mathematical definition of solubility parameters, that it is possible, for example, to achieve the required weighted arithmetic mean solubility parameter, i.e. less than or equal to 10.5, for a hydrophobic carrier comprising two or more substances if one of the substances has an individual solubility parameter greater than 10.5.

Solubility parameters are well known to the formulation chemist of ordinary skill in the art and are routinely used as a guide for determining compatibility's and solubilities of materials in the formulation process.

The solubility parameter of a chemical compound, $\delta$ is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[\frac{\sum_i E_i}{\sum_i m_i}\right]^{1/2}$$

wherein $\Sigma_i$ $E_i$=the sum of the heat of vaporization additive group contributions, and $\Sigma_i$ $m_i$=the sum of the molar volume additive group contributions Standard tabulations of heat of vaporization and molar volume additive group contributions for a wide variety of atoms and groups of atoms are collected in Barton, A. F. M. Handbook of Solubility Parameters, CRC Press, Chapter 6, Table 3, pp. 64–66 (1985), which is incorporated by reference herein in its entirety. The above solubility parameter equation is described in Fedors, F. R., "A Method for Estimating Both the Solubility Parameters and Molar Volumes of Liquids", Polymer Engineering and Science, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, Handbook of Chemistry and Physics, $57^{th}$ edition, CRC Press, p. C-726 (1976–1977), which is incorporated by reference herein in its entirety.

Formulation chemists typically report and use solubility parameters in units of $(cat/cm^3)^{1/2}$. The tabulated values of additive group contributions for heat of vaporization in the Handbook of Solubility Parameters are reported in units of kJ/mol. However, these tabulated heat of vaporization values are readily converted to cal/mol using the following well-known relationships:

1 J/mol=0.239006 cal/mol and 1000 J=1 kJ.

See Gordon, A. J. et al., The Chemist's Companion, John Wiley & Sons, pp. 456–463, (1972), which is incorporated by reference herein in its entirety.

Solubility parameters have also been tabulated for a wide variety of chemical materials. Tabulations of solubility parameters are found in the above-cited Handbook of Solubility Parameters. Also, see "Solubility Effects In Product, Package, Penetration, And Preservation", C. D. Vaughan, Cosmetics and Toiletries, vol. 103, October 1988, pp. 47–69, which is incorporated by reference herein in its entirety.

Nonlimiting examples of hydrophobic carriers include those selected from the group consisting of mineral oil, petrolatum, lecithin, hydrogenated lecithin, lanolin, lanolin derivatives, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cyclomethicones having 3 to 9 silicon atoms, vegetable oils, hydrogenated vegetable oils, polypropylene glycol C4–C20 alkyl ethers, di C8–C30 alkyl ethers, and combinations thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p. 415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, Drug. Cosmet., Ind., 89, 36–37, 76, 78–80, 82 (1961); and International Cosmetic Ingredient Dictionary, Fifth Edition, vol. 1, p. 537 (1993), which are incorporated by reference here in their entirety.

Lecithin is also useful as a hydrophobic carrier. It is a naturally occurring mixture of the diglycerides of certain fatty acids, linked to the choline ester of phosphoric acid.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101 A by Presperse, South Plainfield, N.J.). Also useful are the C7–C40 isoparaffins, which are C7–C40 branched hydrocarbons. Polydecene, a branched liquid hydrocarbon, is also useful herein and is commercially available under the tradenames Puresyn 100® and Puresyn 3000® from Mobile Chemical (Edison, N.J.).

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodedecyl neopentanonoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprylic/capric triglyceride, PEG-6 caprylic/capric triglyceride, PEG-8 caprylic/capric triglyceride, and combinations thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose heptaoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates: behenic of 1:7 to 3:5. A particularly preferred solid sugar polyester is the octaester of sucrose in which there are about 7 behenic fatty acid moieties and about 1 oleic acid moiety in the molecule.

Nonvolatile silicones such as polydialkylsiloxanes, polydiarylsiloxanes, and polyalkarylsiloxanes are also useful oils. The polyalkysiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkysiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_3)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids).

Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl modified siloxanes such as alkyl methicones and alkyl dimethicones wherein the alkyl chain contains 10 to 50 carbons. Such siloxanes are commercially available under the tradenames ABIL WAX 9810 ($C_{24}$–$C_{28}$ alkyl methicone) (sold by Goldschmidt) and SF1632 (cetearyl methicone) (sold by General Electric Company).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Amounts of the oil soluble hydrophobic carrier may range from about 20 to about 99.9%, preferably from about 50 to about 99, more preferably from about 60 to about 95, optimally from about 70 to about 85% by weight of the composition.

Generally, glycols such as propylene glycol and butylene glycol will not be useful as the carriers, especially where they are present in any substantial amount. By this is meant, amounts higher than 50%, or at least amounts higher than 20%, and in some systems in amounts higher than 10% by weight of the composition.

By the term "substantially dry" is meant a composition which has a water content no higher than about 15%, preferably no higher than about 10%, more preferably no higher than about 5%, and optimally between 0 and 4% by weight of the composition.

Another important element of the compositions according to the present invention is that of a water-soluble colorant. A colorant is a material which when placed in water will cause that system to be visually perceivable by a consumer as having a color other than white or cream. Suitable signal colors can be yellow, green, blue, red, orange, black and intermediary shades such as pink. Water-solubility is related to a solubility parameter as discussed above having a value greater than about 10.5, preferably greater than 12.

Amounts of the water-soluble colorant may range from about 0.000001 to about 2%, preferably from about 0.00001 to about 1%, more preferably from about 0.0001 to about 0.5%, even more preferably from about 0.001 to about 0.1%, optimally from about 0.005 to about 0.01% by weight of the composition.

Colorants may be inorganic or organic, with the latter being preferred. Organic colorants include copper salts such as copper sulphate, manganese salts such as potassium permanganate or molybdenum salts such as molybdenum phosphate. Suitable organic colorants are FD&C and D&C dyes. Illustrative are FD&C Blue #1, FD&C Blue #2, FD&C Green #3, FD&C Red #3, FD&C Red #4, FD&C Red #40, FD&C Yellow #5, FD&C Yellow #6, D&C Blue #4, D&C Green #5, D&C Red #6, D&C Red #22, D&C Red #28, D&C Red #33, D&C Yellow #10, Ext D&C Violet #2, Ext D&C Yellow #7, D&C Green #8, D&C Orange #4, D&C Yellow #8, D&C Brown #1, D&C Violet #2 and mixtures thereof. Most preferred is FD&C Green #3.

Although compositions of the present invention may contain components which generate heat upon contact with water (e.g. zeolite), the compositions of the present invention in preferred embodiments do not contain sufficient amounts of these materials to generate any consumer perceivable heat. Likewise, in certain preferred embodiments of the present invention, the compositions will not contain sunscreens in sufficient amount to be legally termed (U.S. FDA-Monograph at 21 CRF 352.10) as a sunscreen product.

Besides the water-insoluble carrier and water-soluble colorants, compositions of the present invention may contain various other types of functional ingredients. These include surfactants, skin benefit agents, thickeners, opacifiers, preservatives, fragrances and mixtures thereof. These materials in total may range in amount from about 0.1 to about 80%, preferably from about 5 to about 60%, more preferably from about 10 to about 40%, optimally from about 15 to about 30% by weight of the composition in total.

Surfactants useful for the present invention may be of the anionic, nonionic, cationic or amphoteric variety as well as combinations thereof. Typical anionic surfactants include salts of acyl isethionates (e.g. sodium cocoyl isethionate), acyl taurates, acyl sarcosinates, acyl lactylates, alkyl ether sulphates, alkyl sulphates and soaps. Useful nonionic surfactants include the $C_{10}$–$C_{20}$ fatty alcohols or acid hydrophobes condensed with from 2 to 100 moles of ethylene oxide or propylene oxide per mole of hydrophobe; $C_2$–$C_{10}$ alkyl substituted phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants. Useful cationic surfactants include trimethyl fatty ammonium salts such as trimethyl stearyl ammonium sulphate. Amphoteric surfactants are illustrated by such materials as cocoamidopropyl betaine and lauroamophoacetates. The amount of surfactant used may range from about 0.01 to about 30%, preferably from about 0.5 to about 10% by weight of the composition.

Skin benefit agents useful in the present invention include alpha and beta hydroxycarboxylic acids as well as their salts and esters, vitamins, lipoic acids, herbal extracts, cationic polymers, self tanning agents, depilatories, skin tightening agents and mixtures thereof. Illustrative alpha-hydroxycarboxylic acids include glycolic acid, malic acid, lactic acid, gluconolactone and mixtures thereof. Salicylic acid is the most preferred beta hydroxycarboxylic acid. Suitable vitamins include the Vitamin A family of retinol, retinyl $C_2$–$C_{20}$ fatty acid esters and retinoic acid; Vitamin B materials such as niacinamide; Vitamin C and its derivatives such as ascorbic acid, ascorbyl tetraisopalmitate, magnesium ascorbyl phosphate and ascorbyl glucoside; Vitamin E such as tocopherol and $C_2$–$C_{20}$ fatty acid tocopherol esters; and folic acid. Cationic polymers most preferred are Polymer JR® and Jaguar C® (e.g. Jaguar C18®). Self-tanning agents principally include dihydroxyacetone. Useful skin tightening agents are kojic acid, resorcinol, arbutin, placental extract, chamomile extract, lactic acid and mixtures thereof. Amounts of the skin benefit agent may range from about 0.00001 to about 15% by weight of the composition.

Thickeners may be included in the compositions at levels from about 0.0001 to about 10%, preferably from about 0.1 to about 1% by weight of the composition. Illustrative materials include $C_{12}$–$C_{24}$ fatty acids, N-fatty glutamic acid dialkylamides, carboxyvinyl polymers such as the Carbomers, polyacrylamides such as Sepiget® 305, taurates, magnesium aluminum silicate (e.g. Veegum®), carboxymethyl cellulose and other cellulose derivatives, aluminum Starch Octenyl Succinates (e.g. Dry Flo®), bentonite clays (e.g. Bentone 38®) and any combinations thereof. Particularly preferred thickeners are stearic acid and N-lauroyl glutamic acid di-N-butylamide.

Opacifiers may also be included in the compositions. These materials may be polyethylene, polystyrenes, polyacrylates, polyamides and copolymers thereof. Most preferred is titanium dioxide, but especially water-dispersible titanium dioxide. Amounts of the opacifiers may range from about 0.001 to about 2% by weight of the composition.

Preservatives useful for the present invention include parabens such as methyl and propyl parabens, and commercially available materials such as Glydant and Glydant Plus®. These may be present in amounts from about 0.0001 to about 1% by weight of the composition.

By the term "personal care" is meant products such as skin cleansers, hair treatments (e.g. shampoos, mousses and conditioners), depilatories, skin lightening products, and leave-on skin lotions and creams. These products may be delivered from wipes (e.g. nonwoven substrates), liquids, gels, pumps or stick format.

All parts, percentages and proportions referred to herein and in the appended claims are by weight unless otherwise illustrated.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

EXAMPLE 1

A typical creamy facial cleanser according to the present invention was formulated with the ingredients reported in Table I below.

TABLE I

| COMPONENT | W/W % |
| --- | --- |
| Mineral Oil | 86.8925 |
| N-lauroyl glutamic acid di-n-butylamide | 1.30 |
| Sodium Cocoyl Isethionate | 10.00 |
| Akogel ® (Hydrogenated vegetable oil) | 1.50 |
| Water Dispersible Titanium Dioxide | 0.50 |
| Hexylene Glycol | 0.50 |
| Fragrance | 0.30 |
| FD&C Green #3 | 0.0075 |

Preparation of the composition in Table I was as follows. N-lauroyl glutamic acid di-N-butylamide, sodium cocoyl isethionate and hydrogenated vegetable oil were added to a reactor filled with the mineral oil. Continuous mixing occurred while the components were added and simultaneously the temperature was increased to reach 135° C. Thereafter mixing was maintained but heat removed and the composition allowed to cool. Titanium dioxide was then dispersed within the hexylene glycol with vigorous agitation. When the main reactor containing the mineral oil composition reached a temperture less than 40° C., the titanium dioxide-hexylene glycol dispersion, as well as colorant and fragrance were added to the reactor. After a 5 minute agitation, the process was complete.

The composition of Table I is applied by a consumer to the face. Water is then added and the mixture rubbed into the skin. Gradually the formula turns blue-green indicating that actives have been released to the skin.

EXAMPLE 2

Another example of a creamy cleanser is outlined by the formula in Table II.

TABLE II

| COMPONENT | W/W % |
|---|---|
| Mineral Oil | 74.4925 |
| Sodium Stearate | 4.00 |
| Sodium Cocoyl Isethionate | 20.00 |
| Water Dispersible Titanium Dioxide | 0.50 |
| Hexylene Glycol | 0.50 |
| Fragrance | 0.50 |
| FD&C Green #3 | 0.0075 |

The composition of Table II was prepared in a manner similar to that described under Example 1. The only difference was that sodium stearate and sodium cocoyl isethionate were added to the mineral oil as a first step.

EXAMPLE 3

As a comparative example there was prepared the formula outlined in Table III.

TABLE III

| COMPONENT | W/W % |
|---|---|
| Butylene Glycol | 74.4925 |
| Sodium Stearate | 4.00 |
| Sodium Cocoyl Isethionate | 20.00 |
| Water Dispersible Titanium Dioxide | 0.50 |
| Hexylene Glycol | 0.50 |
| Fragrance | 0.50 |
| FD&C Green #3 | 0.0075 |

Unlike Example 2 which before wetting was white in color, the composition of Table III before being wetted was colored green. Butylene glycol is a carrier which does solubilize the FD&C Green #3 and therefore is not a carrier (as mineral oil is) which can mask color until activated by addition of water.

EXAMPLE 4

This Example illustrates a depilatory composition (Table IV) employing the color change of the present invention.

TABLE IV

| COMPONENT | W/W % |
|---|---|
| Silicone Oil | 88.9925 |
| Sodium Stearate | 4.00 |
| Thioglycolic Acid | 5.00 |
| Fragrance | 1.00 |
| Water Dispersible Titanium Dioxide | 0.50 |
| Hexylene Glycol | 0.50 |
| FD&C Red #40 | 0.0075 |

EXAMPLE 5

This Example illustrates an anti-acne composition whose ingredients are listed in Table V.

TABLE V

| COMPONENT | W/W % |
|---|---|
| Petrolatum | 94.9925 |
| Salicylic Acid | 4.00 |
| Water Dispersible Titanium Dioxide | 0.50 |
| Hexylene Glycol | 0.50 |
| FD&C Blue #1 | 0.0075 |

EXAMPLE 6

This Example illustrates a color changing cleanser.

TABLE VI

| COMPONENT | WEIGHT % |
|---|---|
| Mineral Oil | 48.72 |
| Compritol 888 ATO ® (Glycerol Dibehenate EP-Glyceryl Behenate) | 7.28 |
| Sodium Cocoyl Isethionate | 15.00 |
| Sodium Aluminosilicate (Anhydrous) | 24.70 |
| Shea Butter | 4.00 |
| Fragrance | 0.20 |
| Alpha Bisabolol | 0.10 |
| FD&C Green #3 | 0.0040 |

The formulation is prepared by charging a reactor with mineral oil. Into the reactor are added Compritol 888 ATO®, sodium cocoyl isethionate, sodium aluminosilicate and shea butter. While mixing heat is applied eventually reaching 130° C. Thereafter, heat is removed and the composition allowed to cool. When the temperature has dipped below 40° C., the colorant, alpha-bisabolol and fragrance are dosed to the reactor. After a 5 minute agitation, the product is ready for use.

EXAMPLE 7

This Example illustrates another type of cleanser. The formulation is listed in Table VII.

TABLE VII

| COMPONENT | WEIGHT % |
|---|---|
| Mineral Oil | 23.8820 |
| Versagel 1600 ® | 18.03 |
| Sodium Lauryl Sulfoacetate (65% Active) | 9.95 |
| Sodium Aluminosilicate (Anhydrous) | 44.50 |
| Shea Butter | 2.13 |
| Water Dispersible Titanium Dioxide | 0.60 |
| Hexylene Glycol | 0.60 |
| Fragrance | 0.20 |
| Alpha Bisabolol | 0.10 |
| FD&C Green #3 | 0.0040 |

A reactor is charged with the mineral oil. Into the reactor is added the Versagel 1600®, the sodium lauroyl sulfoacetate powder, sodium aluminosilicate and shea butter. Reactants are mixed while temperature is increased to 130° C. Thereafter the resultant mixture is allowed to cool with continuous agitation. Upon reaching 40° C., the reactor is further charged with the colorant, alpha-bisabolol, a dispersion of titanium dioxide in hexylene glycol, and fragrance. Agitation is continued for another 5 minutes whereupon the blend becomes ready for use.

EXAMPLE 8

This Example illustrates still another type of cleanser. The formulation is listed in Table VIII.

TABLE VIII

| COMPONENT | WEIGHT % |
|---|---|
| Mineral Oil | 72.7960 |
| Performalene 400 Polyethylene ® (Polyethylene) | 8.00 |
| Performacid 350 Acid ® ($C_{20}$–$C_{40}$ Acid and Polyethylene) | 4.00 |
| Sodium Lauryl Sulfoacetate (65% Active) | 15.00 |
| Fragrance | 0.20 |
| FD&C Red #40 | 0.0040 |

A reactor was charged with the mineral oil. While applying heat and mixing, the further ingredients were added including the Performalene 400 Polyethylene®, Performacid 350 Acid® and sodium lauryl sulfoacetate. Upon achieving 135° C. temperature, heat was removed and the mixture allowed to cool while agitation was maintained. Upon the temperature leveling below 40° C., the colorant and fragrance was added followed by 5 minutes of agitation.

EXAMPLE 9

This Example illustrates yet another type of cleanser. The formulation is listed in Table IX.

TABLE IX

| COMPONENT | WEIGHT % |
|---|---|
| Sunflowerseed Oil | 76.2960 |
| Sodium Cocoyl Isethionate | 20.00 |
| Sodium Stearate | 3.50 |
| Fragrance | 0.20 |
| FD&C Red #40 | 0.0040 |

Sunflowerseed oil was placed in a reactor and heated with mixing to 130° C. During the temperature rise, the reactor was further charged with the sodium cocoyl isethionate and sodium stearate. Heat was then removed from the blend while continuous agitation was maintained. Upon the reactor composition falling below 40° C., the colorant and fragrance were added. Agitation was continued for 5 minutes to ensure thorough mixing of all components.

EXAMPLE 10

This Example illustrates another type of cleanser. The formulation is listed in Table X.

TABLE X

| COMPONENT | WEIGHT % |
|---|---|
| Shinetsu KSG-15 ® (Cyclopentasiloxane and Dimethicone/Vinyl Dimethicone Crosspolymer) | 87.196 |
| Hamposyl L-94 ® (Sodium Lauroyl Sarcosinate, 94%) | 5.00 |
| Tegobetaine CKD ® (Cocoamidopropyl Betaine, 94%) | 4.00 |
| Polyglyceryl 6 Laurate | 3.00 |
| Hexylene Glycol | 0.10 |
| Titanium Dioxide | 0.10 |
| Polyquaternium 7 | 0.20 |
| Fragrance | 0.20 |
| Retinyl Palmitate | 0.10 |
| Tocopheryl Acetate | 0.10 |
| FD&C Green #3 | 0.004 |

The process procedure was essentially identical with that described in Example 1, except that all ingredients were sequentially added to the Shinetsu KSG-15® component.

EXAMPLE 11

This Example illustrates another type of cleanser. The formulation is listed in Table XI.

TABLE XI

| COMPONENT | WEIGHT % |
|---|---|
| Shinetsu KSG-15 ® (Cyclopentasiloxane and Dimethicone/Vinyl Dimethicone Crosspolymer) | 87.596 |
| Thioglycolic Acid | 7.00 |
| Calcium Hydroxide | 5.00 |
| Fragrance | 0.20 |
| Retinyl Palmitate | 0.10 |
| Tocopheryl Acetate | 0.10 |
| FD&C Green #3 | 0.004 |

The process procedure was essentially identical with that described in Example 1, except that all ingredients were sequentially added to the Shinetsu KSG-15® component.

The foregoing description and examples illustrate selected embodiments of the present invention. In light thereof variations and modifications will be suggested to one skilled in the art, all of which are within the spirit and purview of this invention.

What is claimed is:

1. A personal care substantially dry composition comprising:
   (i) from about 0.000001 to about 2% by weight of the composition of a colorant activatable by water to reveal a visual color, the colorant not being encapsulated and requiring no physical breakdown of encapsulating walls for activation; and
   (ii) from about 20 to about 99.9% by weight of the composition of an oil-soluble carrier, wherein the colorant is insoluble in the carrier and the visual color is not imparted to the composition in its substantially dry state.

2. A composition according to claim 1 wherein the oil-soluble carrier is selected from the group consisting of hydrocarbons, $C_1$–$C_{30}$ esters of carboxylic acids, vegetable oils, silicones and combinations thereof.

3. The composition according to claim 1 wherein the oil-soluble carrier is present in an amount from about 60 to about 95% by weight of the composition.

4. The composition according to claim 1 wherein the colorant is present in an amount from about 0.0001 to about 0.5% by weight of the composition.

5. The composition according to claim 1 wherein the visual color imparted is other than white.

6. The composition according to claim 1 which is a product selected from the group consisting of skin cleanser, hair treatment, depilatory and skin lightening product.

7. The composition according to claim 1 further comprising a nonwoven substrate onto which the composition is impregnated.

8. The composition according to claim 1 wherein the composition in its substantially dry state is white in color resulting from the presence of titanium dioxide.

9. The composition according to claim 1 further comprising a water dispersible titanium dioxide in an amount from about 0.001 to about 2% by weight of the composition.

10. A personal care substantially dry composition comprising:
    (i) from about 0.0001 to about 0.5% by weight of the composition of a water-soluble colorant activatable by water to reveal a visual color, the colorant not being encapsulated and requiring no physical breakdown of encapsulating walls for activation; and
    (ii) from about 20 to about 99.9% by weight of the composition of an oil-soluble carrier having a solubility parameter value of greater than 10.5;

wherein the colorant is insoluble in the carrier and the visual color is not imparted to the composition in its substantially dry state.

11. The composition according to claim 10 wherein the oil-soluble carrier is present in an amount from about 60 to about 95% by weight of the composition and is selected from the group consisting of hydrocarbons, $C_1$–$C_{30}$ esters of carboxylic acids, vegetable oils, silicones and combinations thereof.

12. The composition according to claim 1 wherein the oil-soluble carrier has a solubiliry parameter value of greater than 10.5.

13. The composition according to claim 1 not containing sunscreen agents in sufficient amount to serve as a sunscreen product.

14. A personal care substantially dry composition comprising:
(i) from about 0.00000 1 to about 2% by weight of the composition of a colorant activatable by water to reveal a visual color; and
(ii) from about 60 to about 99.9% by weight of the composition of an oil-soluble carrier selected from the group consisting of hydrocarbons, $C_1$–$C_{30}$ esters of carboxylic acids, vegetable oils, silicones and combinations thereof, wherein the colorant is insoluble in the carrier and the visual color is not imparted to the composition in its substantially dry state.

* * * * *